US012778807B2

(12) United States Patent
Donnellan et al.

(10) Patent No.: US 12,778,807 B2
(45) Date of Patent: Nov. 3, 2026

(54) DRESSING DEVICE FOR USE WITH A CANNULA OR A CATHETER

(71) Applicant: Bard Access Systems, Inc., Salt Lake City, UT (US)

(72) Inventors: Peter Donnellan, County Limerick (IE); Marie N. Ni Beiliu, County Louth (IE); Keith Real, County Wicklow (IE)

(73) Assignee: Bard Access Systems, Inc., Salt Lake City, UT (US)

( * ) Notice: Subject to any disclaimer, the term of this patent is extended or adjusted under 35 U.S.C. 154(b) by 667 days.

(21) Appl. No.: 17/706,355

(22) Filed: Mar. 28, 2022

(65) Prior Publication Data

US 2022/0241112 A1 Aug. 4, 2022

Related U.S. Application Data

(62) Division of application No. 16/512,157, filed on Jul. 15, 2019, now abandoned, which is a division of (Continued)

(51) Int. Cl.

*A61F 13/00* (2024.01)
*A61L 15/26* (2006.01)
*A61L 15/46* (2006.01)

(52) U.S. Cl.

CPC ........ *A61F 13/00063* (2013.01); *A61L 15/26* (2013.01); *A61L 15/46* (2013.01);

(Continued)

(58) Field of Classification Search

None

See application file for complete search history.

(56) References Cited

U.S. PATENT DOCUMENTS 4,221,215 A 9/1980 Mandelbaum
4,339,550 A * 7/1982 Palinczar ................ A61L 9/042 521/159

(Continued)

FOREIGN PATENT DOCUMENTS

WO 2007/127236 A2 11/2007
WO 2008/010199 A2 1/2008

(Continued)

OTHER PUBLICATIONS

Bhende et al. "In vitro assessment of chlorhexidine gluconate-impregnated polyurethane foam antimicrobial dressing using zone of inhibition assays" Aug. 2004.

(Continued)

*Primary Examiner* — Isis A Ghali
(74) *Attorney, Agent, or Firm* — Rutan & Tucker LLP

(57) ABSTRACT

A dressing device and a method of making the dressing device is disclosed. For example, the method can include forming a polyurethane foam, adhering a moisture vapor-transmissive backing to the polyurethane foam, and cutting the polyurethane foam with the moisture vapor-transmissive backing thereon to form the dressing device. Notably, forming the polyurethane foam can include mixing together a polyurethane prepolymer and an aqueous mixture of chlorhexidine di-gluconate and polyanhydroglucuronic acid or a salt of polyanhydroglucuronic acid in a first reaction vessel until a homogenous mixture is formed; dispensing the homogenous mixture onto a liner; and allowing the homogenous mixture to expel carbon dioxide. Upon expelling the carbon dioxide, the polyurethane foam is formed with the chlorhexidine di-gluconate and the polyanhydroglucuronic acid or the salt of polyanhydroglucuronic acid homogenously dispersed throughout the polyurethane foam.

12 Claims, 7 Drawing Sheets

Related U.S. Application Data application No. 13/808,183, filed as application No. PCT/IE2011/000034 on Jul. 4, 2011, now abandoned.

(60) Provisional application No. 61/344,403, filed on Jul. 14, 2010.

(52) U.S. Cl.
CPC ... *A61L 2300/206* (2013.01); *A61L 2300/232* (2013.01); *A61L 2300/404* (2013.01); *A61L 2300/418* (2013.01); *A61L 2300/45* (2013.01); *A61L 2400/04* (2013.01)

(56) References Cited

U.S. PATENT DOCUMENTS

| | | | | |
|---|---|---|---|---|
| 4,941,882 | A | 7/1990 | Ward et al. | |
| 5,064,653 | A * | 11/1991 | Sessions | C08G 18/10 424/404 |
| 5,571,529 | A * | 11/1996 | Cheong | C08G 18/4837 424/443 |
| 6,093,465 | A | 7/2000 | Gilchrist et al. | |
| 6,596,293 | B1 | 7/2003 | Bootman et al. | |
| 2003/0093115 | A1 | 5/2003 | Levinson | |
| 2005/0003178 | A1* | 1/2005 | Detert | C09J 5/00 428/317.1 |
| 2008/0027365 | A1 | 1/2008 | Huey | |
| 2020/0069475 | A1 | 3/2020 | Donnellan et al. | |

FOREIGN PATENT DOCUMENTS

| | | | |
|---|---|---|---|
| WO | 2008/0101199 | A1 | 8/2008 |
| WO | 2008104276 | A1 | 9/2008 |

OTHER PUBLICATIONS

Bjornson, H., et al., "Association between microorganism growth at the catheter insertion site and colonization of the catheter in patients receiving total parenteral nutrition" Surgery, 92(4): pp. 720-727 (1982).

Bouza, E., et al., "Catheter-related infections: diagnosis and intravascular treatment" Clin. Microbial. Infect. 8: 265- 274 (2002).

Doerfler, M., et al., "Central venous catheter placement in patients with disorders of hemostasis" Chest 110 (1) pp. 185-188 (1996).

Haemostatic Agents for Topical Use (1977).

Lee, R., et al., "A Clinical Study of the Coagulation Time of Blood" J. Am. Med. Sci., vol. 245 (4), pp. 495-503 (Apr. 1913).

Maki, D., et al., "Infections due to infusion therapy" Taken from: Bennett J V, Brachman P S, eds. Hospital Infections. Philadelphia, Pa: Lippincott-Raven; pp. 689-724 (1998).

Maki, D., et al., "Novel Integrated Chlorhexidine-impregnated Transparent Dressing for Prevention of Vascular Catheter-related Bloodstream Infection: A Prospective Comparative Study in Healthy Volunteers", Poster Presentation at the Society for HealthCare Epidemiology of America Conference , Orlando, Fla. (2008).

Maki, D., et al., "Prevention of central venous catheter-related bloodstream infection by use of an antiseptic-impregnated catheter. A randomized, controlled trial" Ann Intern Med, 127(4): pp. 257-266 (1997).

Milstone et al. "Chlorhexidine: Expanding the Armamentarium for Infection Control and Prevention", Clinical Infectious Disease; 46:274-281. (Year: 2008).

Mital, A., et al., "Bleeding Complications associated with peritoneal dialysis catheter insertion," Peritoneal Dialysis Int. 24 pp. 478-480 (2004).

PCT/IE2011/000034 filed Apr. 7, 2011 International Search Report and Written Opinion dated Sep. 26, 2011.

Raad, I., et al., "Diagnosis of Catheter-Related Bloodstream Infections: Is it necessary to culture the subcutaneous catheter segment?" Eur. J. Clin. Microbial. Infect. Dis. 20 pp. 566-568 (2001).

Safdar, N., et al., "The pathogenesis of catheter-related bloodstream infection with noncuffed short-term central venous catheters" Intensive Care Med, 30(1): pp. 62-67 (2004).

Sherertz, R., et al., "Diagnosis of triple-lumen catheter infection: Comparison of roll plate, sonication and flushing methodologies" J. Clin. Microbial. 35 pp. 641-646 (1997).

Suetens, C., et al., "European surveillance of ICU-acquired infections (HELICS-ICU): methods and main results," Journal of Hospital Infection 65 pp. 171-173 (2007).

Timsit, J., "Diagnosis and prevention of catheter-related infections" Curr. Opin. Crit. Care 13 (5) pp. 563-571 (2007).

U.S. Appl. No. 13/808,183, filed Jan. 3, 2013 Advisory Action dated Nov. 9, 2016.

U.S. Appl. No. 13/808,183, filed Jan. 3, 2013 Examiner's Answer dated Apr. 17, 2017.

U.S. Appl. No. 13/808,183, filed Jan. 3, 2013 Final Office Action dated Aug. 12, 2015.

U.S. Appl. No. 13/808,183, filed Jan. 3, 2013 Final Office Action dated Aug. 30, 2016.

U.S. Appl. No. 13/808,183, filed Jan. 3, 2013 Non-Final Office Action dated Feb. 2, 2016.

U.S. Appl. No. 13/808,183, filed Jan. 3, 2013 Non-Final Office Action dated Mar. 6, 2015.

U.S. Appl. No. 16/512,157, filed Jul. 15, 2019 Final Office Action dated Dec. 29, 2021.

U.S. Appl. No. 16/512,157, filed Jul. 15, 2019 Final Office Action dated Feb. 10, 2021.

U.S. Appl. No. 16/512,157, filed Jul. 15, 2019 Non-Final Office Action dated Aug. 18, 2020.

U.S. Appl. No. 16/512,157, filed Jul. 15, 2019 Non-Final Office Action dated Jul. 26, 2021.

* cited by examiner

DRESSING DEVICE FOR USE WITH A CANNULA OR A CATHETER

PRIORITY

This is a division of U.S. patent application Ser. No. 16/512,157, filed Jul. 15, 2019, which is a division of U.S. patent application Ser. No. 13/808,183, filed Jan. 3, 2013, which is a U.S. national stage application of International Application No. PCT/IE11/00034, filed Jul. 4, 2011, claiming the benefit of priority to U.S. Provisional Application No. 61/344,403, filed Jul. 14, 2010, each of which is hereby incorporated by reference in its entirety into this application.

INTRODUCTION

The present invention relates to a wound device, particularly for use with IV catheters and other percutaneous devices.

Vascular and nonvascular percutaneous medical devices such as: IV catheters, central venous lines, arterial catheters, dialysis catheters, peripherally inserted coronary catheters, mid-line catheters, drains, chest tubes, externally placed orthopedic pins, and epidural catheter tubes are widely used in modern day medical practice. Annually more than 20 million inpatients in hospitals in the United States receive intravenous therapy and almost 5 million require central venous catheterization (Bouza et al., 2002)

Mechanical complications such as hemorrhage and thrombosis are associated with catheterization. The risk of bleeding associated with catheterization is reported to range between 1% and 8% (Mital et al., 2004) and although minor bleeding may be quite common serious bleeding is rare (Doerfler et al. 1996). Though dressings for antimicrobial effectiveness have long been available no product deals sufficiently with the bleeding from these wound types and this leads to dressing changes being a regular occurrence. There remains a need for an effective dressing for use with IV catheters that stops bleeding and is an effective antimicrobial solution.

Catheter use causes a semi-permanent breach of the skin that provides an access point for pathogens to enter the body, placing the patient at risk for local and systemic infectious complications. The potential for infection may be increased by proliferation of bacteria within or underneath the dressing. Studies have shown that between 5% and 25% of IV devices are colonized at the time of removal (Maki et al., 1998). Skin flora is the main source of microbial contamination and is responsible for approximately 65% of catheter related infections. Bacteria from the skin migrate along the external surface of the catheter and colonize the intravascular catheter tip leading to catheter related blood stream infections (Raad et al., 2001; Sheretz et al., 1997). Catheter-related bloodstream infection (CR-BSI) is the third most common health care-acquired infection in the United States and is considered one of the most dangerous complications for patients. In Europe the incidence and density of central venous catheter (CVC) related bloodstream infections ranges from 1-3.1 per 1000 patient days (Suetens et al., 2007). Most organisms responsible for CR-BSIs originate from the insertion site of the catheter (Timsit, 2007), therefore, decreasing bacterial colonization at the site of insertion may help reduce the incidence of CR-BSIs.

It is an object of the current invention to provide an improved wound dressing device that will provide protection at an insertion site.

SUMMARY OF THE INVENTION

According to the invention there is provided a dressing device for use with a transcutaneous medical device such as a cannula or a catheter, the dressing device comprising a flexible hydrophillic polyurethane matrix, an antimicrobial agent contained within the matrix, and a hemostatic agent contained within the matrix, the hemostatic agent comprising polyanhydroglucuronic acid or salt thereof in an amount to achieve a hemostatic effect, and the antimicrobial agent comprising chlorhexidine di-gluconate in an amount to achieve an antimicrobial effect without adversely affecting wound healing.

The invention provides a wound dressing device that prevents microbial colonization of the dressing and stops bleeding from the insertion site. The device provides combined hemostatic and antimicrobial effects at the insertion site but without adversely affecting wound healing.

This is a particularly surprising aspect of the invention because a dressing composition that contains only polyanhydroglucuronic acid or salt thereof to promote wound healing and hemostasis is not conducive to contamination and infection control. The addition of chlorhexidine di-gluconate as an antimicrobial agent effective at preventing contamination and infection would be expected to adversely affect wound healing. We have surprisingly found that this is not the case.

The polyanhydroglucuronic salt may be present in an amount of from 3% to 20% (w/w). The polyanhydroglucuronic salt may for example be present in an amount of approximately 8% w/w.

The chlorhexidine di-gluconate may be present in an amount of from 9% to 16% (w/w). The chlorhexidine di-gluconate may for example be present in an amount of approximately 11% w/w.

In one embodiment the dressing device comprises approximately 8% (w/w) polyanhydroglucuronic acid, approximately 11% (w/w) chlorhexidine di-gluconate, and approximately 81% hydrophillic flexible polyurethane foam.

In one embodiment the dressing device comprises an aperture for reception of a medical device such as a cannula or a catheter.

In one embodiment the dressing device comprises a breathable backing material to allow vapor transmission from the device.

A skin contacting side of the device may contain an adhesive compound to keep the device affixed to a site.

In one case the central access aperture is a circular hole ranging in size from 0.1 mm to 10 mm in diameter.

Alternatively the central access aperture is "x" shaped.

The central access aperture may be "T" shaped.

In one embodiment the device contains a quantity of the antimicrobial agent to maintain antimicrobial efficiency for up to 7 days.

The invention in one aspect is an absorbent polymeric wound dressing containing a broad spectrum antimicrobial agent and a hemostatic agent with a moisture vapor permeable backing and radial slit and central access hole to allow insertion of an IV catheter line or other similar percutaneous device. The device contains sufficient quantities of the broad spectrum antimicrobial agent to ensure that a clear antimicrobial zone of inhibition can be maintained around the insertion site and to prevent microbial contamination of the dressing. The device also contains sufficient quantities of hemostatic agent in order to successfully control minor bleeding at the insertion site.

The absorbent polymer foam matrix dressing of the invention rapidly addresses bleeding, prevents dermal wound site contamination and infection while at the same time promoting wound healing. Rapid wound healing and closure in a controlled aseptic (near microbe free) environment provides the optimal conditions for reduced wound site morbidity.

The absorbent polymer foam matrix dressing composition of the invention addresses the paradoxical requirement of good antimicrobial efficacy, good hemostatic efficacy and good wound healing properties in the same absorbent, conformable polymer foam composition containing specific narrow range non-antagonistic concentrations of antimicrobial, hemostatic and wound healing agents that allow for combined effective interactions that are antimicrobial, hemostatic and wound healing.

A specific application of the present invention relates to a wound device, particularly for use with IV catheters and other percutaneous devices.

The invention disclosure described herein identifies a novel device composition which allows for the singular important advantage in being able to attain antimicrobial, hemostatic and wound-healing promoting characteristics in a single absorbent and compliant device system. Normally achieving such functional heterogeneity in one device is not possible due to antagonistic effects of the separate functions on one another. The unique feature of this invention is that it is able to identify and integrate effective ranges for each active component without adversely affecting the functions of the other components.

BRIEF DESCRIPTION OF THE DRAWINGS

The invention will be more clearly understood from the following description of an embodiment thereof, given by way of example only, with reference to the accompanying drawings, in which.

DETAILED DESCRIPTION OF THE INVENTION

Figure 1:
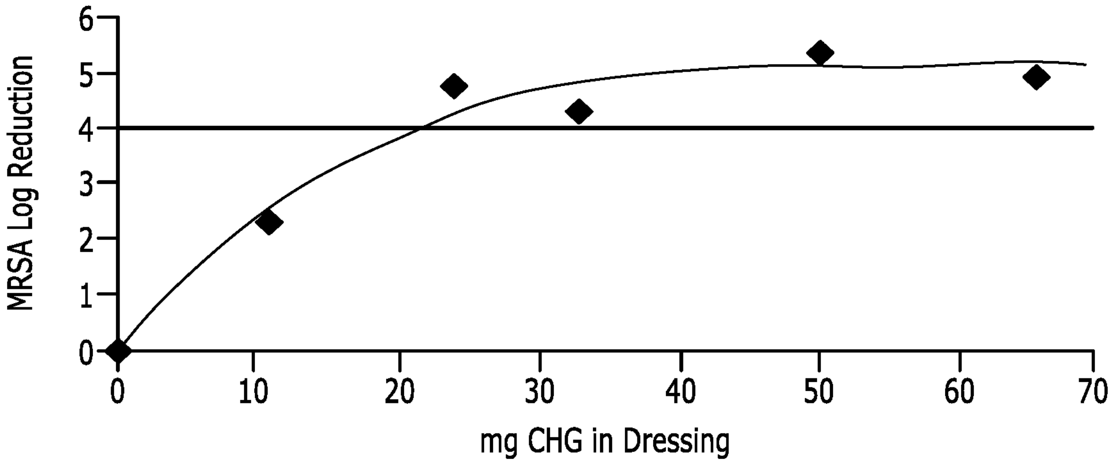
FIG. 1 shows the results of the antimicrobial testing against methicillin-resistant *Staphylococcus aureus* (MRSA) using AATCC Test Method 100-2004 after 24 hours incubation of sterilized polyurethane foam matrix dressings containing polyanhydroglucuronic acid calcium sodium salt (8% w/w) dressing with increasing weight percent of chlorhexidine di-gluconate (CHG) in a 217 mg, 25 mm diameter dressing.

The invention provides wound dressings for controlling minor bleeding at the access sites of IV catheters and similar percutaneous devices. Moreover the invention provides protection at the access site and contains a broad spectrum antimicrobial agent to help resist microbial colonization of the dressing. The device also successfully reduces bleeding time. The dressing device provides advantages over other IV site dressings as it contains a hemostatic agent.

In one embodiment of the invention polyanhydroglucuronic acid is incorporated into the polymeric base material as the hemostatic agent and chlorhexidine di-gluconate is incorporated as the broad spectrum antimicrobial agent.

The device may have a moisture vapor permeable backing to allow for moisture transmission. The backing may, for example, comprise a thin polyurethane film.

The system of the present invention has been shown to effectively maintain antimicrobial efficacy over a period of up to 7 days.

On complete saturation with an aqueous medium the absorption capacity of the foam of the present invention is typically greater than 8 times (wt/wt relative to the dry weight of the dressing). Preferred absorption capacity of the dressing is 10 to 15 times (wt/wt).

In one embodiment of the system the polymeric base material is polyurethane foam. The components that make up the system may be present in the system with final concentrations of, for example, 8% (w/w) polyanhydroglucuronic acid 11% (w/w) chlorhexidine di-gluconate and 81% hydrophillic flexible polyurethane foam.

The dressings of the invention will generally be sterile. Sterilization may be carried out using gamma irradiation but other sterilization methods such as ethylene oxide sterilization may also be used.

In one embodiment, the dressing device has an adhesive technology on the skin contacting surface to aid in site securement and also for removal and re-securement.

In one embodiment the wound dressing is circular with an outer diameter of 0.6 to 2 inches (1.52 to 5.08 cm). The outer diameter may be about one inch (2.54 cm). The dressing of the invention will typically have a central access aperture to facilitate passage of an IV catheter line or other similar percutaneous device.

In other embodiments the central access aperture may be “x” or “T” shaped. One embodiment of the device has a circular cut central access site. The size of the central access site may vary from typically 1 mm to 10 mm.

In further embodiments of the invention the device may be non-circular.

Having described the invention in general terms, reference is now made to specific non-limiting examples.

The invention provides a hemostatic and wound healing promoting antimicrobial dressing for general wound use, but also particularly for controlling minor bleeding at the access sites of IV catheters and similar percutaneous devices. Moreover the invention promotes wound healing while providing protection at the access site by slow release of a broad-spectrum antimicrobial agent to help resist microbial colonization of the dressing. The device also successfully reduces bleeding time. The antimicrobial hemostatic dressing device described herein provides significant advantages over prior art dressing forms as it provides for wound healing in combination with hemostasis and contamination and infection control while avoiding antagonism between pro-healing, hemostatic and antimicrobial elements.

Example 1

Hemostatic and Antimicrobial Polyurethane Foam Preparations

To prepare hemostatic and antimicrobial foam the hemostat polyanhydroglucuronic acid (PAGA) (HemCon Medical Technologies Europe Ltd, Dublin) and the antimicrobial compound chlorhexidine di-gluconate (CHG) (Kapp Technologies LLC, New Jersey) were used. Polyurethane foam dressings were prepared with varying concentrations of PAGA and CHG relative to the final dry weight of polyurethane foam. The polyurethane foam used is type MS50P(w) Lendell medical foam available from Filtrona Porous Technologies (www.filtronaporoustechnologies.com)

| | |
|---|---|
| Usable Width: | 15 inches (381 mm) |
| Thickness: | 0.22 inches (5.6 mm) |
| % Moisture: | 2% |
| Density: | 6.0 pcf (96 Kg/m$^3$) |
| Tensile Strength: | 51.0 psi (352 kPa) |
| Target Elongation: | 194% |
| Tear Strength: | 5.6 pli (0.98 kN/m) |
| CDF@50%: | 0.74 psi (5.14 kPa) |
| Durometer: | 47 shore |
| Cell Size: | 131 ppi |
| Absorption: | 15 g/g |
| Expansion | 75% |
| Wrung Retention: | 1.2 g/g |

The polyurethane foam was produced by firstly producing a prepolymer comprising a poly-isocyanate [OCN—R—NCO]$_n$ and dial [OH—R—OH] which were mixed in a pre-polymer reaction vessel. The components of the pre-polymer were mixed together using agitation in a mechanical mixer for over ten minutes ensuring that all components were thoroughly mixed. The polyurethane polymerisation reaction occurred in the pre-polymer mixing vessel. In a separate vessel the PAGA and CHG were blended together in a vessel containing only water and surfactant with continual mixing until a homogenous suspension had been achieved. Unlike other hemostats the PAGA hemostat had the solubility and viscosity characteristics that allow for aqueous mixing and it additionally demonstrates chemical inertness towards the CHG and silver entities to allow such aqueous phase preparation. The water content of the aqueous phase ranged up to 300% stoichiometric equivalents to the pre-polymer. Surfactants chosen from the group silicone oils, polydimethylsiloxane-polyoxyalkylene block copolymers, nonylphenol ethoxylates, or other similar acting organic compounds used for the dual purpose of acting as anti-foaming compounds in the aqueous phase while regulating the correct cell size and structure and overall physical appearance of the foam. The aqueous phase containing the actives and the reacted prepolymer mix were then both independently pumped to a third vessel where they were physically mixed by mechanical means ensuring a homogenous mixture. The pre-polymer and aqueous phase mixture was then dispensed from the mixing vessel onto a conveyer belt coated with a carrier liner to prevent adherence to the belt. The water of the aqueous phase reacted with the isocyanate groups of the pre-polymer and $CO_2$ gas was expelled which caused the foam to rise to desired height 0.375 inches. The polyurethane foam was then covered with a nitrogen blanket to prevent further reaction and allowed to cure and dry for 24-72 hrs. A number of different formulations were prepared for manufacturing suitability. The formulations with the impregnated components are outlined in Table 1.

TABLE 1

Prepared foam formulations

| PAGA (w/w %) | CHG (w/w %) | Polyurethane (w/w %) |
|---|---|---|
| 15 | 30 | 55 |
| 15 | 22.5 | 62.5 |
| 15 | 15 | 70 |
| 15 | 7.5 | 68.5 |
| 15 | 5 | 80 |
| 11.25 | 22.5 | 66.25 |
| 7.5 | 15 | 68.5 |
| 3.75 | 7.5 | 88.25 |

Example 2

Antibacterial Efficacy of Prepared Formulations Calcium Sodium Salt Polyanhydroglucuronic Acid and Chlorhexidine Di-Gluconate in a Polyurethane Foam Polyurethane foam matrix dressings were prepared with the calcium sodium salt of polyanhydroglucuronic acid (15% w/w) and w/w percentages of CHG at 0%, 5%, 11%, 15%, 23% and 30% as presented in Example 1. These formulations were investigated for their antibacterial efficacy against methicillin-resistant *Staphylococcus aureus*

(MRSA) using AATCC Test Method 100 "Assessment of Antibacterial Finishes on Textiles".

Analysis of FIG. 1 indicates that the acceptable minimum low range of chlorhexidine di-gluconate percentage weight fraction in the polyurethane foam matrix is 9% (20 mg) to 16% (35 mg) w/w since this range achieves the acceptable >Log 4 reduction.

The results for gamma-irradiated sterilized testing and non-gamma-irradiated testing are presented in Table 2.

TABLE 2

Formulations of PAGA impregnated PU foam with increasing CHG concentrations

| CHG | 5% (w/w) | 11% (w/w) | 15% (w/w) | 23% (w/w) | 30% (w/w) |
|---|---|---|---|---|---|
| Log Reduction (Sterile) | 2.3 | >4.7 | 5.3 | >5.4 | >5.0 |
| Log Reduction (Non-sterile) | 2.7 | >5.2 | >5.3 | >5.4 | 5.3 |

Example 3

Device Assembly

A catheter access site dressing device to control bleeding was prepared by impregnating calcium sodium salt of poly-anhydroglucuronic acid into polyurethane foam. CHG was incorporated to achieve an antimicrobial efficacy of greater than 4 log in 24 hours. A formulation as described in Table 3 was prepared and a moisture vapor permeable backing that comprised of polyurethane film with a MVTR of 1000 $gm/m^2/24$ hour (3M) was adhered.

TABLE 3

IV site device composition

| Ingredients | Formulation (% w/w) final formulation |
|---|---|
| Chlorhexidine gluconate | 11 |
| Calcium-sodium polyanhydroglucuronic acid | 8 |
| Hydrophillic flexible polyurethane foam | 81 |

The polyurethane foam matrix was die cut into 25. mm diameter disks with a central 4 mm diameter section removed from each disk. A radial slit was also punched from the center of the disk to the outside of the disk. The slit and 4 mm punch are designed to allow catheter access. The dressing is sterilized by gamma irradiation between 25 and 45 kGy, sufficient to produce a sterility assurance limit (SAL) of $10^{-6}$.

The device described was tested for antimicrobial efficacy against a number of micro-organisms including gram positive and gram negative bacteria, fungi and yeast. The antimicrobial efficacy was tested using the AATCC Test Method 100 "Assessment of Antibacterial Finishes on Textiles". In summary 1.0 ml of test organism suspension at a minimum of $1\times10^6$ CFU/ml was inoculated to the test sample. At selected time points (time zero and 24 hours) organisms were extracted in a neutralizer media (D/E broth) which was diluted and plated. Log reduction and percent reduction were determined. The results obtained are shown in Table 4.

TABLE 4

Antimicrobial results of the IV site device

| Micro-organism | Decrease of CFU number/ 24 hours |
|---|---|
| *Staphylococcus aureus* | >4 log |
| *Staphylococcus epidermidis* | >4 log |
| *Enterococcus faecium* | >4 log |
| *Escherichia coli* | >4 log |
| *Pseudomonas aeruginosa* | >4 log |
| *Acinetobacter baumanii* | >4 log |
| *Klebsiella pneumoniae* | >4 log |
| *Candida albicans* | >4 log |
| *Aspergillus niger* | >4 log |

Example 4

In Vitro Hemostatic Efficacy

The device described in Example 3 was tested for its ability to activate the intrinsic blood coagulation cascade, specifically coagulation factor XIIa and kallikrein. In summary, 0.5 $cm^2$ of the device and also a control device which was another polyurethane IV site device but without poly-anhydroglucuronic acid (1" DISK, 4.0 mm centre hole with radial slit and containing 92 mg CHG (Biopatch; Ethicon)), were placed in Eppendorfs. 0.25 ml of deionized $H_2O$ was added to the dressings and incubated at room temperature for 10 min. After 10 min incubation, the dressings were compressed and the fluid supernatant removed. Subsequently, 45 ul of the fluid supernatant was added to fresh Eppendorfs. Then 90 ul of deionized $H_2O$ was added along with 45 ul of normal coagulation control plasma. The samples were mixed and incubated at room temperature for 10 min. After the incubation stage 40 ul of each sample were added to microtiter plate wells and 40 ul of 0.8 mM S-2302 (specific Factor XIIa and kallikrein chromogenic substrate) was then added to initiate the reaction. The reaction was allowed to proceed for 3 minutes and then the optical density at 405 nm was read. The results for this study are presented in Table 5.

TABLE 5

Activation of Factor XIIa and kallikrein

| Sample | Mean Optical Density @ 405 nm (3 min read) | Activity Rate/min |
|---|---|---|
| PAGA containing PU Foam IV device | 53.40 | 17.80 |
| Other non PAGA containing PU Foam IV device | 0 | 0 |

The control IV site dressing not containing PAGA did not activate the coagulation factor XIIa and kallikrein of the intrinsic coagulation system. The device described by Example 3 did activate the intrinsic coagulation enzymes. Such activation is consistent with oxidized cellulose mechanism of action and this demonstrated the potential of the device to be a hemostat.

Example 5

Hemostatic Efficacy—In Vivo Measurements

Having established the potential for hemostatic activity in Example 4 the device was tested for hemostatic activity in a suitable in vivo bleeding model. Devices of the formulation as described in Example 3 were tested for their hemostatic efficacy in vivo in a rabbit ear model.

The study was divided in two periods. Within the first test period (D+1) the Test Item was tested on the left ear of the rabbit, the right ear was used as control. Within the second period (D+3) the Test Item was tested on the right ear of the rabbit, the left ear was used as a control. Bleeding was caused by puncture of a lateral ear vein with an injection needle (external diameter always 0.9 mm). On D+1 the puncture was performed at an acral part of the ear, on D+3 the puncture was performed cranially. Distance between both punctures was 2-3 cm. The test and control were applied immediately after the puncture wounds were made. Test items and controls were weighed before their use and immediately after cessation of bleeding. Also the time from start to the end of bleeding was measured.

In this study wounds treated with the Test Item bled for a shorter period of time and had a smaller blood loss compared to the control (Pur-Zellin® cellulose swab, HARTMANN-RICO a.s.) thereby demonstrating the hemostatic efficacy of the device. Data demonstrating the in vivo hemostatic efficacy of the device is outlined in Table 7.

TABLE 11

Results for the device in time to stop bleeding and blood loss mass

| | Test Item (n = 16) | Control (n = 16) |
|---|---|---|
| Average quantity of Absorbed Blood (g) | 0.167 ± 0.18 | 1.311 ± 1.08 |
| Average Time of Bleeding (seconds) | 48.8 ± 20.1 | 89.4 ± 77.4 |

Example 6

Wound Healing

The effect on wound healing of the device prepared with the composition of Example 3 was assessed on dermal wound healing in two separate in vivo studies on rats.

Dressings prepared with the composition of Example 3 were assessed in vivo for their effect on dermal wound healing in rats. Each of twelve animals received three dorsal full thickness wounds created with an 8 mm dermal punch. Following wound creation the wound was covered with a test sample, a control dressing (non PAGA containing IV site dressing as in Example 4) or left untreated. The wound sites on each animal were covered with a secondary dressing. Animals were observed daily to ensure integrity of the wound, to observe signs of general clinical health and to record wound measurements. The same dressing that was removed was replaced on the wound after each measurement had been taken. Dressings were changed as necessary depending on the degree of saturation with exudate and wear time was limited to a maximum of 7 days exposure of a single treatment on the wound.

Figure 5:
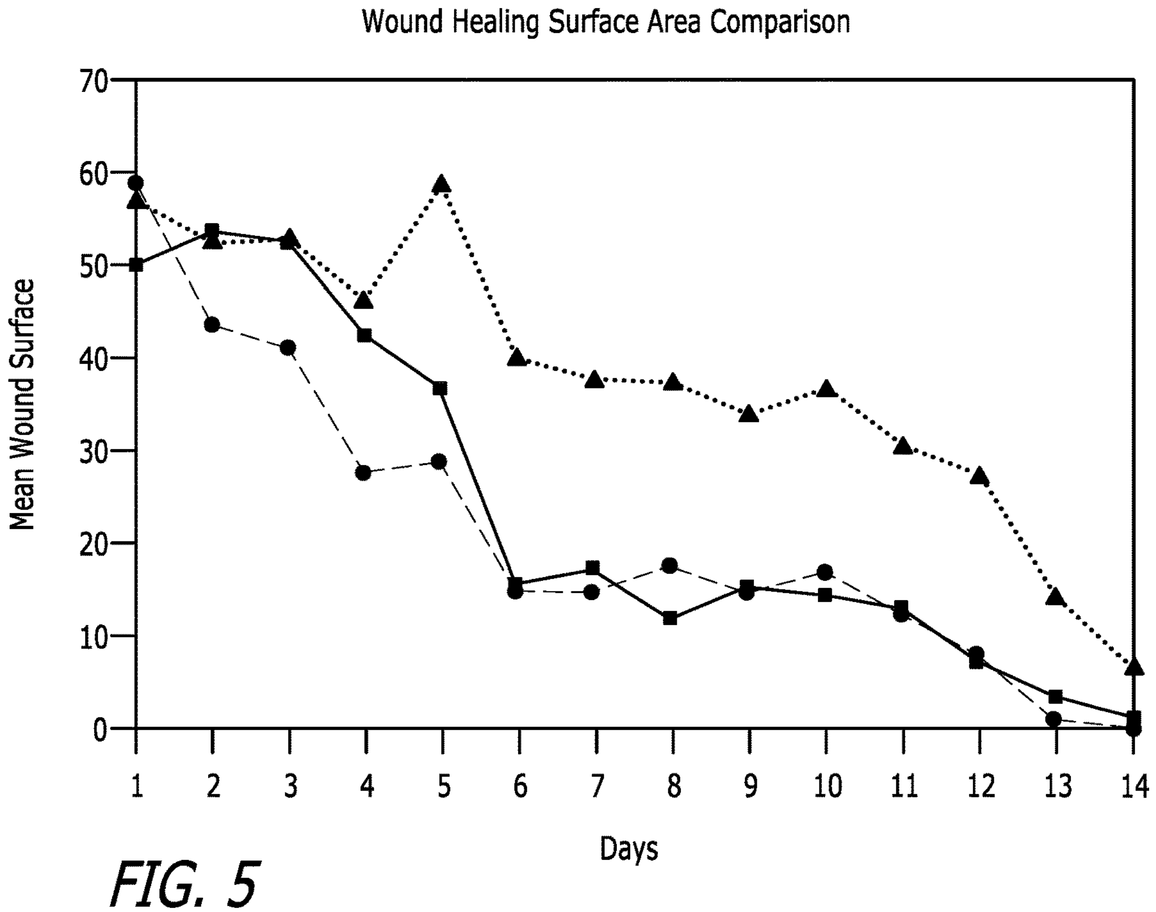
FIG. 5 compares mean wound surface area in a study 1 of an untreated control (dashed line (- - - ) un-treated wounds), a test item (solid line - wounds treated with the test dressing device of Example 3), and a control dressing (dotted line ( . . . ))

All wounds healed comparably by day 14 with the test article of the composition of Example 3 performing between the untreated wound (see FIG. 5) and the control dressing. However, it could be seen that during the mid-stage of the study the animals from the control dressing group showed slower dermal healing compared to the described device and the negative control. This can be attributed to the significantly higher CHG content (92 mg/dressing or 30% (w/w)) of the control dressing.

Example 7

Further Wound Healing and Oedema Formation

Dressings prepared with the composition of Example 3 were assessed in vivo for their effect on dermal wound healing in rats in an experiment similar to that described in Example 6. Each of ten animals received three dorsal full thickness wounds to the depth of the subcutis created with a 10 mm dermal punch. Following wound creation each of the three wound on each animal was covered with either a test sample, a control dressing (non PAGA containing IV site dressing as in Example 4 and 6) or left untreated. The wound sites on each animal were covered with a secondary dressing. Animals were observed daily to ensure integrity of the wound, to observe signs of general clinical health and to record wound measurements. The same dressing that was removed was replaced on the wound after each measurement had been taken. Dressings were changed as necessary depending on the degree of saturation with exudate and wear time was limited to a maximum of 7 days exposure of a single treatment on the wound. The wounds were also evaluated for signs of erythema and oedema.

Figure 6:
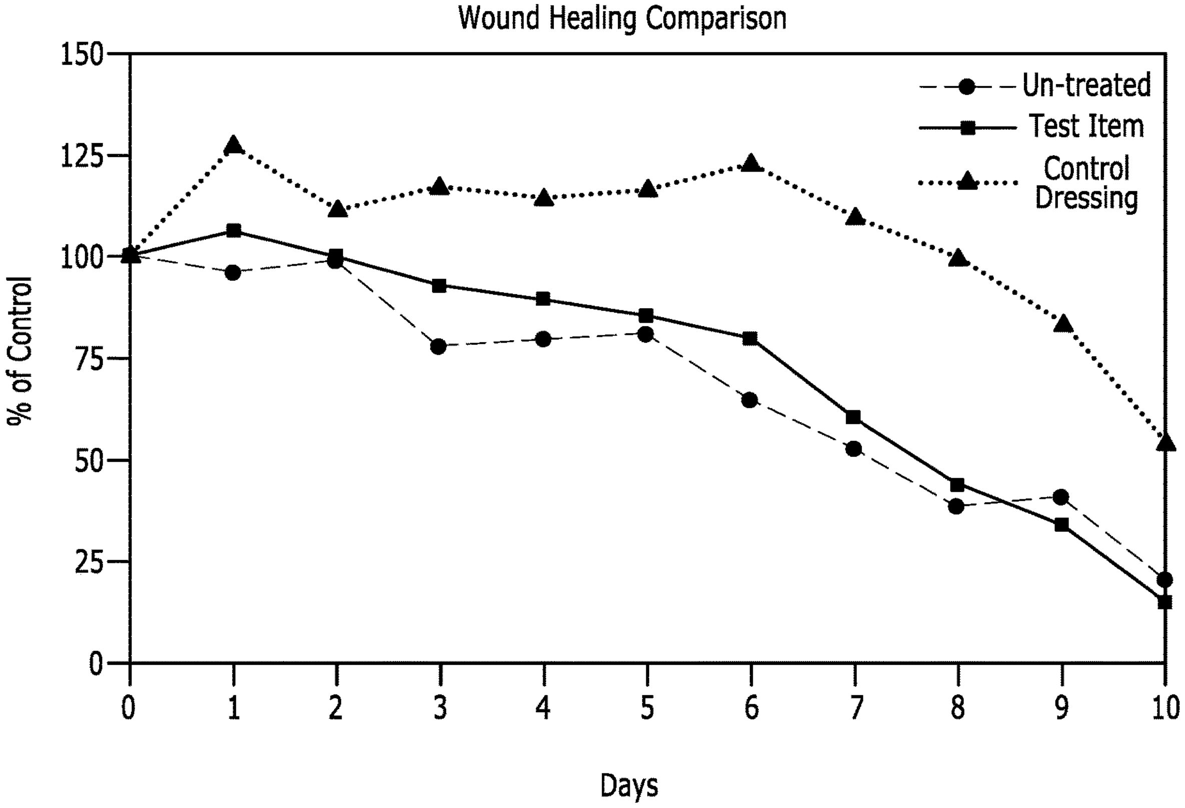
FIG. 6 demonstrates the change in wound surface area of an untreated control (dashed line (- - - ) un-treated wounds), a test item (solid line - wounds treated with the test dressing device of Example 3), and a control dressing (dotted line ( . . . a))
Figure 7:
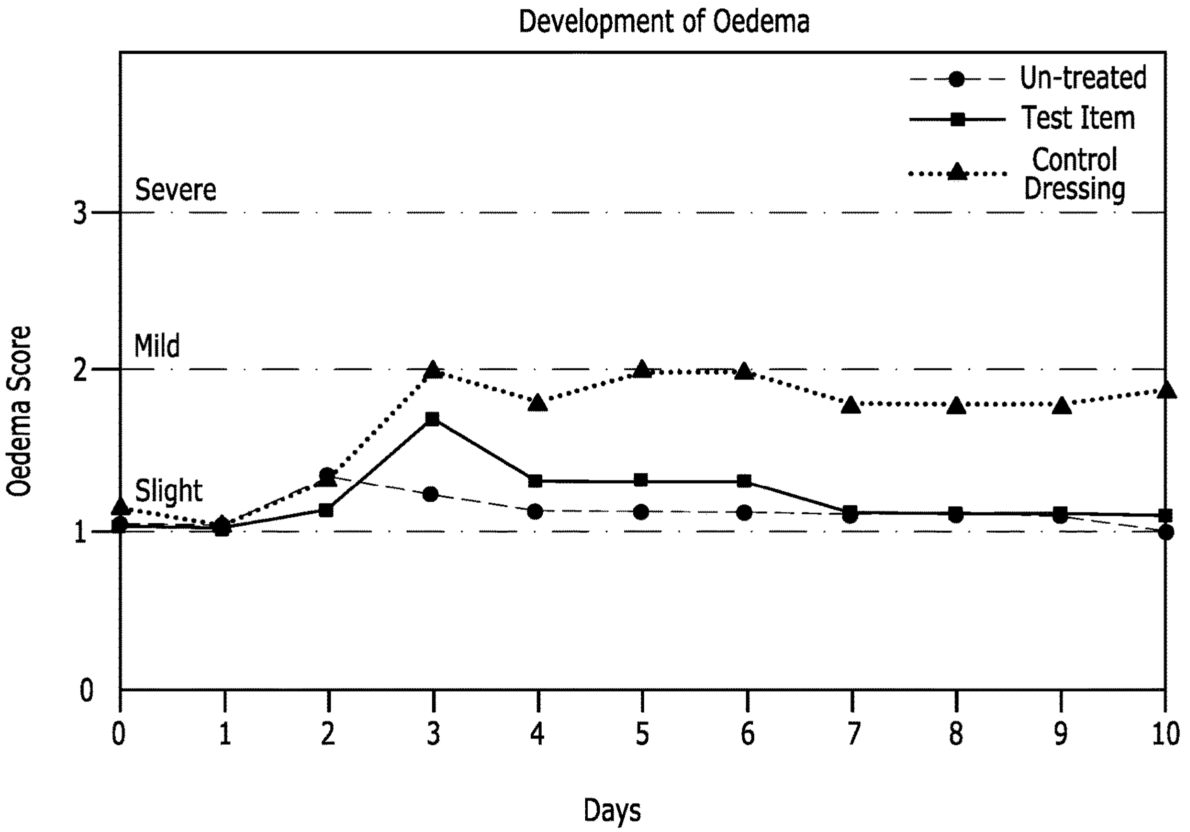
FIG. 7 demonstrates oedema development of an untreated control (dashed line (- - - ) un-treated wounds), a test item (solid line - wounds treated with the test dressing device of Example 3), and a control dressing (dotted line ( . . . ))
Figure 8A:
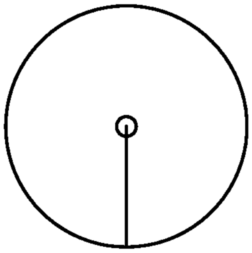
FIGS. 8(*a*) to 8(*h*) illustrates some different physical embodiments of a wound dressing device of the invention.
Figure 8B:
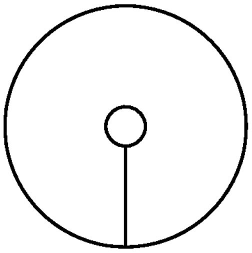
Figure 8C:
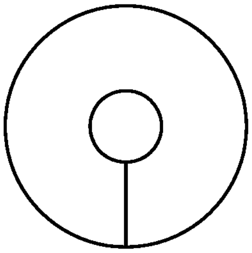
Figure 8D:
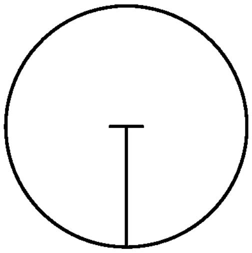
Figure 8E:
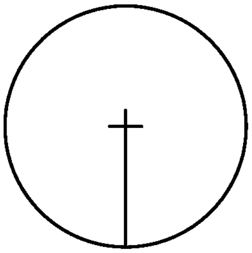
Figure 8F:
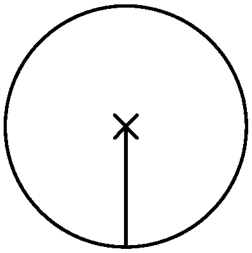
Figure 8G:
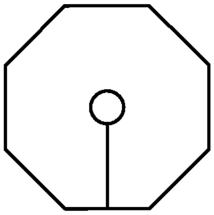
Figure 8H:
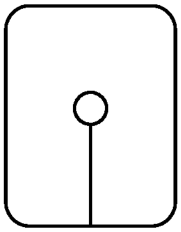
Figure 9A:
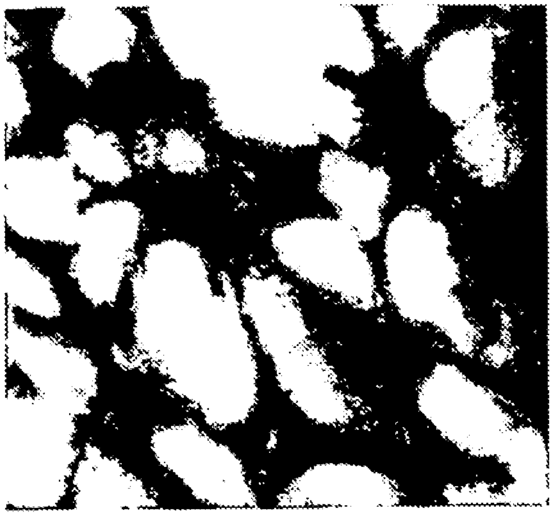
FIGS. 9(*a*) to 9(*b*) shows representative micrographs of polyurethane foam A) without the impregnation of haemostatic calcium sodium polyanhydroglucuronic acid and B) with the impregnation of calcium sodium polyanhydroglucuronic acid. The apparatus in FIG. 9(*b*) indicate particles of calcium-sodium polyanhydroglucuronic acid.
Figure 9B:
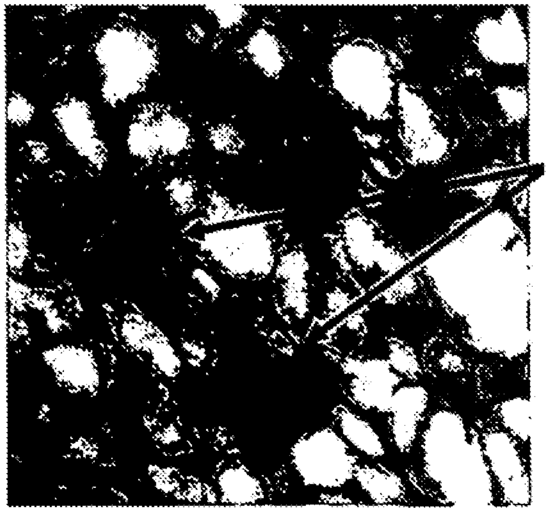

As with the study described in FIGS. 9(*a*) and 9(*b*) all wounds healed comparably by day 10 with the test article of the composition of Example 3 performing between the untreated wound and control dressing (See FIG. 6). There were no visible signs of erythema development at any of the wound sites (Table 12). Slight oedema formation was reported for untreated wounds and those treated with the test item (FIG. 7 and Table 13). In general a similar response was observed for un-treated wounds and wounds treated with the test item. Oedema formation was more pronounced in wounds treated with the control dressing which contained a significantly higher fraction of CHG (30% w/w).

Generally, untreated wounds and wounds treated with the test item healed in similar manners. Both healed at a faster rate than wounds treated with control dressing and the higher CHG concentration. Also Oedema formation was less pronounced in these wounds compared to wounds treated with control dressing. The less favorable wound healing results seen for the control dressing can be attributed to the higher CHG content (30% w/w).

TABLE 12

Erythema Formation
Erythema Average Score

| | Day | | | | | | | | | | |
|---|---|---|---|---|---|---|---|---|---|---|---|
| | 0 | 1 | 2 | 3 | 4 | 5 | 6 | 7 | 8 | 9 | 10 |
| Un-treated | 1 | 0 | 0 | 0 | 0 | 0 | 0 | 0 | 0 | 0 | 0 |
| Test Item | 1 | 0 | 0 | 0 | 0 | 0 | 0 | 0 | 0 | 0 | 0 |
| Control Dressing | 1 | 0 | 0 | 0 | 0 | 0 | 0 | 0 | 0 | 0 | 0 |

Key:
(0 = Normal (no erythema), 1 = Slight erythema, 2 = Mild erythema, 3 = Severe ertherma)

TABLE 13

| Oedema Development Oedema Average Score | Day | | | | | | | | | | |
|---|---|---|---|---|---|---|---|---|---|---|---|
| | 0 | 1 | 2 | 3 | 4 | 5 | 6 | 7 | 8 | 9 | 10 |
| Un-treated | 1 | 1 | 1.3 | 1.2 | 1.1 | 1.1 | 1.1 | 1.1 | 1.1 | 1.1 | 1 |
| Test Item | 1 | 1 | 1.1 | 1.7 | 1.3 | 1.3 | 1.3 | 1.1 | 1.1 | 1.1 | 1.1 |
| Control Dressing | 1.1 | 1 | 1.3 | 2 | 1.8 | 2 | 2 | 1.8 | 1.8 | 1.8 | 1.9 |

Key:
(0 = Normal (No oedema), 1 = Slight oedema, 2 = Mild oedema, 3 = Severe oedema)

Example 8

Sustained Antimicrobial Efficacy-Log Reduction

To demonstrate the sustained antimicrobial efficacy of was dressing formulation in example 3 over 24 hours and 7 days, AATCC Test Method 100-2004 "Assessment of Antimicrobial Finishes on Textiles" was used. The results of this testing (Table 14) demonstrate that the formulation in example 3 is highly effective in controlling a broad range of gram negative and gram positive bacteria as well as the fungi *C. albicans* and *A. niger*. Also a modified version of the AATCC Test Method 100 was investigated. In the modified AATCC 100 test method, in addition to testing dressing samples following 24 hour exposure to the test organisms, reference and test dressings are also exposed for 6 days to a mock wound environment that potentially could lead to loss or degradation of the antimicrobial activity. Following the 6-day exposure, the dressings are inoculated and the test conducted according to the standard AATCC Test Method 100. Dressing were tested against a number of micro-organisms including gram positive and gram negative bacteria and dimorphic fungi/yeast. The log reduction data observed following 24 hours and 7 days is outlined in Table 15 below. A log reduction of greater than 4 log was recorded for each of the test organisms demonstrating the sustained antimicrobial activity of the antimicrobial agent in the dressing.

TABLE 14

Standard AATCC antimicrobial finish testing

| Micro-organism | 24 hrs Log Reduction | 7 days Log Reduction |
|---|---|---|
| *Staphylococcus aureus* CCM 7110 | 5.50 | 6.31 |
| *Staphylococcus epidermidis* CCM 7221 | 5.53 | 6.18 |
| *Enterococcus faecium* CNCTC 5773 | 5.52 | 5.51 |
| *Escherichia coli* CCM 4517 | 5.58 | 6.38 |
| *Pseudomonas aeruginosa* CCM 1961 | 5.76 | 6.70 |
| *Acinetobacter baumanii* CNCTC 6168 | 5.55 | 6.16 |
| *Klebsiella pneumoniae* CCM 4415 | 4.83 | 6.62 |
| *Candida albicans* CCM 8215 | 4.72 | 4.71 |
| *Aspergillus niger* | 4.20 | 4.19 |

TABLE 15

Modified AATCC antimicrobial finish testing

| Micro-organism | 7 days Log Reduction |
|---|---|
| *Staphylococcus aureus* CCM 7110 | >4 |
| *Staphylococcus epidermidis* CCM 7221 | >4 |
| *Enterococcus faecium* CNCTC 5773 | >4 |
| *Escherichia coli* CCM 4517 | >4 |
| *Pseudomonas aeruginosa* CCM 1961 | >4 |
| *Acinetobacter baumanii* CNCTC 6168 | >4 |
| *Klebsiella pneumoniae* CCM 4415 | >4 |
| *Candida albicans* CCM 8215 | >4 |
| *Aspergillus niger* | >4 |

Example 9

Sustained Antimicrobial Efficacy—Zone of Inhibition

Figure 2:
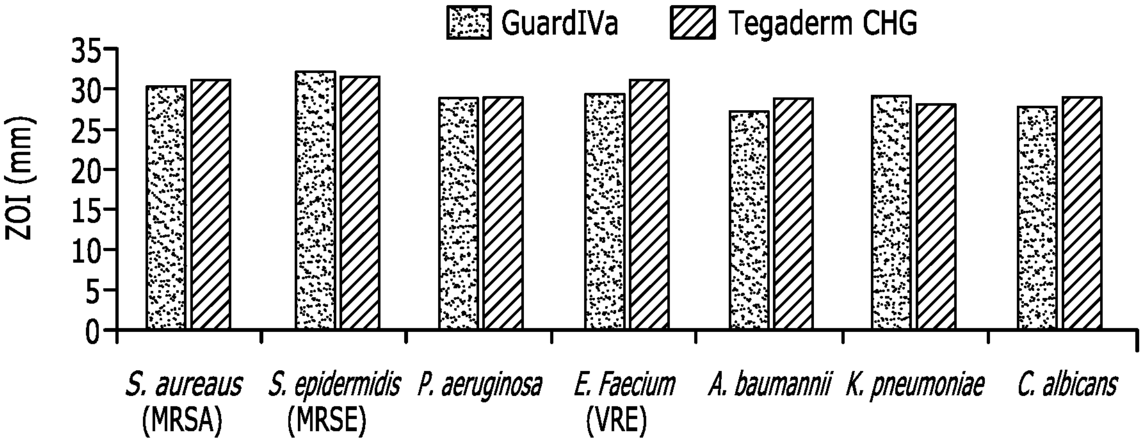
FIG. 2 shows results of Kirby Bauer antimicrobial zone of inhibition testing after 24 hours incubation for the polyurethane foam matrix described in example 3 and a commercially available chlorhexidine di-gluconate containing matrix control material (intended to reduce catheter related blood stream infection) against methicillin resistant *Staphylococcus aureus* (MRSA), methicillin resistant *Staphylococcus epidermidis* (MRSE), *Pseudomonas aeruginosa*, vancomycin resistant *Enterococcus faecium* (VRE), *Acinetobacter baumannii, Klebsiella pneumoniae* and *Candida albicans;*
Figure 3A:
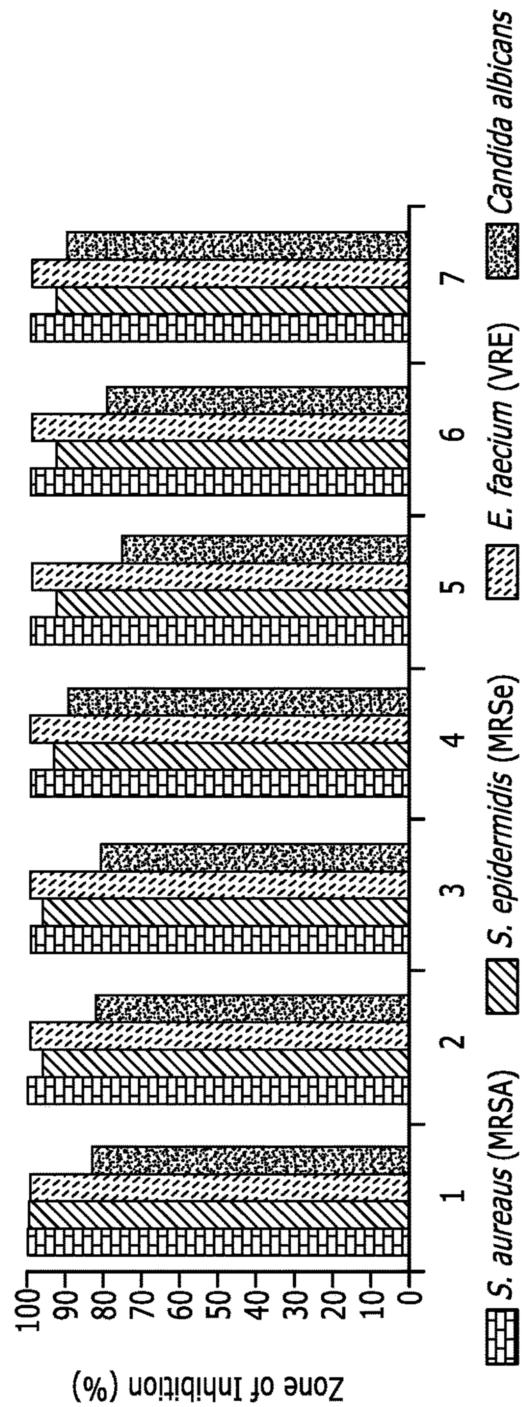
FIGS. 3A-3B show results of Kirby Bauer antimicrobial zone of inhibition testing after 1, 2, 3, 4, 5, 6 & 7 days for the polyurethane foam matrix described in example 3 against the gram positive organisms (FIG. 3A) methicillin resistant *Staphylococcus aureus* (MRSA), methicillin resistant *Staphylococcus epidermidis* (MRSE), vancomycin resistant *Enterococcus faecium* (VRE) and the fungus and *Candida albicans*, and against gram negative organisms (FIG. 3B) *Escherichia coli, Pseudomonas aeruginosa, Acinetobacter baumannii* and *Klebsiella pneumoniae;*
Figure 3B:
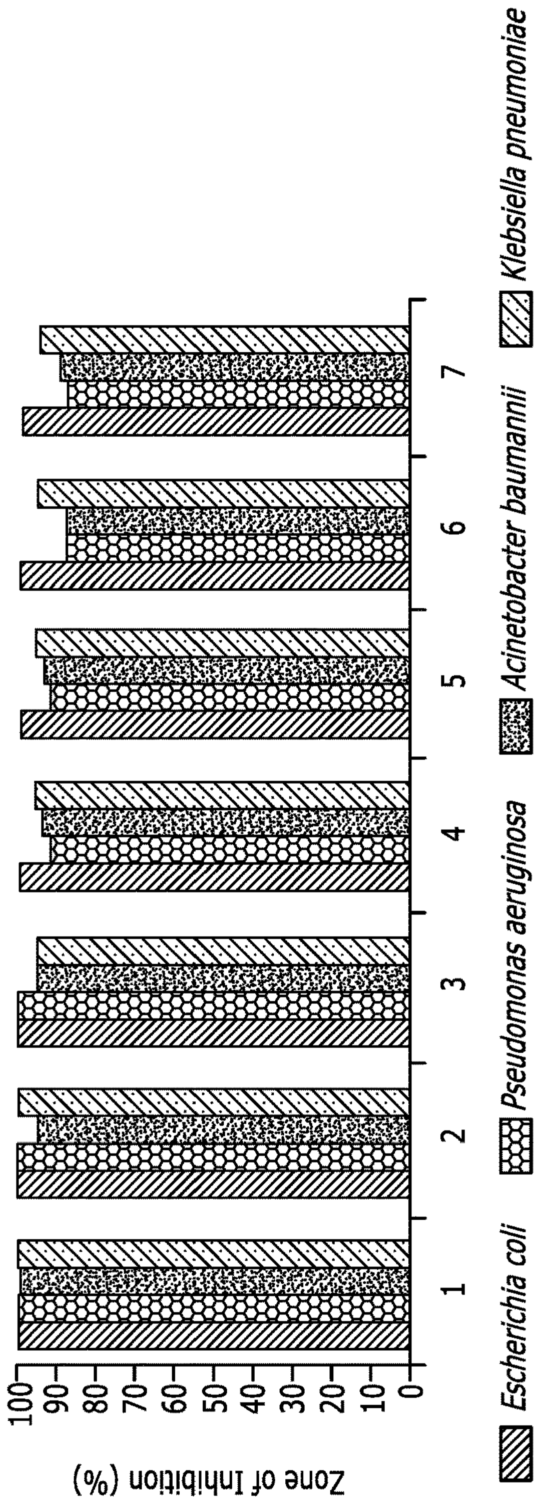

A Kirby-Bauer Zone of Inhibition method was used to investigate the sustained antimicrobial efficacy of the dressing in Example 3 over 24 hours and 7 days. Overnight cultures were prepared to a minimum inoculum count of 1×107 CFU/ml and spread on freshly prepared agar plates. An individual test article was placed onto the agar plate and incubated for 24 hrs at 35-37° C. The area under the test article was swabbed and the swab was transferred onto sterile agar plates. The test article was then placed on a freshly inoculated agar plate and the procedure repeated. The test articles were transferred each day for up to seven days. Growth from the swabs taken from the test articles indicated bacteriostatic action of the antimicrobial agent while no growth indicated bactericidal action. Samples were tested in triplicate. The bactericidal or bacteriostatic action of the dressing at 7 days is shown in Table 16. FIG. 2 shows zone of inhibition results at 24 hours while FIGS. 3A & 3B show the zone of inhibition % changes at 1, 2, 3, 4, 5, 6 & 7 days.

TABLE 16

Bacteriocidal or Bacteriostatic action of the device

| Micro-organism | Bacteriocidal or Bacteriostatic |
|---|---|
| *Staphylococcus aureus* CCM 7110 | Bacteriocidal |
| *Staphylococcus epidermidis* CCM 7221 | Bacteriocidal |
| *Enterococcus faecium* CNCTC 5773 | Bacteriocidal |
| *Escherichia coli* CCM 4517 | Bacteriocidal |
| *Pseudomonas aeruginosa* CCM 1961 | Bacteriostatic |
| *Acinetobacter baumanii* CNCTC 6168 | Bacteriostatic |
| *Klebsiella pneumoniae* CCM 4415 | Bacteriocidal |
| *Candida albicans* CCM 8215 | Bacteriostatic |

Example 10

A Prospective Human Clinical Study of Suppression of Skin Microflora

The primary objective of this study was to investigate the ability of the polyurethane foam matrix dressing formulation of example 3 to suppress the regrowth of skin microflora following skin preparations on healthy human volunteers. This study was performed on healthy human volunteers following the method of Maki et al. 2008. The study was independently conducted by the Center for Laboratory Activities in Public Health Protection and Promotion, National Reference Laboratory for Disinfection and Sterilization, National Institute of Health, Prague, Czech Republic.

Subjects—A group of 12 study subjects was selected and enrolled for testing through informed consent. All were Caucasian with an average age of 52.5 years and an age range between 25 years and 69 years. This study was conducted to assess the capacity of the test dressings (example 3 formulation) to suppress skin flora re-growth following skin prepping for 1 minute with 70% isopropyl alcohol when compared to an inactive control dressing. Each subject served as his or her own control by using 8 randomized sites in the subclavian area of each volunteer. On study day 0, baseline skin flora counts were established from randomized sites. Skin flora count from these randomized sites was also measured following air drying immediately post-prep with 70% isopropyl alcohol. Once the remaining sites had air-dried immediately post-prep, the test dressings (example 3 formulation) and the control dressings (polyurethane foam with no CHG or oxidized cellulose) were applied to the remaining prepped sites of the subjects. Dressings were applied to the subclavian sites using sterile tweezers and attached by latex-free, hypoallergenic and transparent polyurethane securement dressings. The dressings were left up to 10 days, and skin flora counts were taken at 7 and 10 day time points. Skin flora was measured using standard scrubbing techniques and the skin flora beneath the dressing quantitated through use of a recovery solution that was then cultured on agar plates. Wilcoxon paired tests were used for statistical testing of the level of significance (P-values<0.05 were considered significant).

Figure 4:
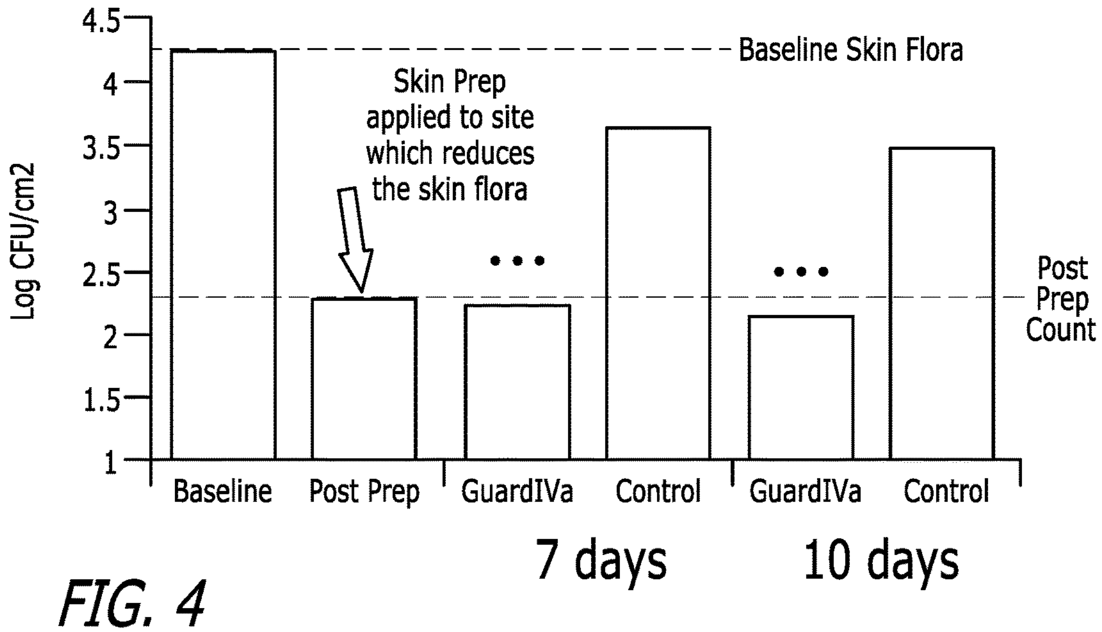
FIG. 4 shows the results of testing of suppression of re-growth of human skin microflora on prepped subclavian sites for the polyurethane foam matrix described in example 3 in healthy volunteers (N=12). The method of testing was based on that described by Maki et al 2008. The control dressing is polyurethane foam matrix with no chlorhexidine di-gluconate and no polyanhydroglucuronic acid. Bacterial counts are expressed as log 10 CFU/cm$^2$. There is a statistically significant difference ($P<0.001$) between test and control dressings at both day 7 and day 10. Skin prepping was carried out for 1 minute with 70% isopropyl alcohol.

Disinfection of the skin prior to catheter insertion provides substantial protection to a site, but viable bacteria may still remain on the skin and re-grow over time, thus leading to a greater possibility of infection. Any catheter related bloodstream infection preventive strategy should be able to reduce skin microbial colonization for the duration of the catheter insertion. The results seen in FIG. 4 show the effect of the 70% isopropyl alcohol skin prep. The raw skin flora counts were dramatically reduced, as would be expected. It can also be observed that after both the 7 day and 10 day time points, the test dressings maintained the skin flora at levels equivalent to those of the post-prep level, whereas with the control dressings significant skin flora re-growth was evident. Bacterial counts were converted to log 10 CFU/cm2 prior to statistical analysis. At day 7, the test dressings showed significantly lower skin flora counts post-prep compared to the control dressings which had substantial re-growth (P<0.001). At day 10, test dressings also showed significantly lower re-growth (P<0.001). As can be seen (FIG. 4), the test dressing maintained the skin flora count at less than the post-prep count for the complete duration of the study out to 10 days.

No adverse events, such as skin irritation, edema or erythema formation were reported for the study with the test dressing. The test dressing successfully and significantly prevented the re-growth of microorganisms for up to 10 days as demonstrated by this study. After both 7 and 10 days, the microbial count was seen to be less than that of the post-prep microbial count. As such, it would be expected that the test dressing formulation (example 3) would be an effective component of a strategy to reduce skin microbial colonization. From literature, such a reduction in skin colonization markedly reduces the risk of catheter related bloodstream infection [Bjornson et al. 1982, Safdar et al. 2004, Maki et al. 1997].

Example 11

Different Physical Embodiments

The produced PAGA and CHG impregnated foam described in Example 3 was also die cut into different sized and shaped devices. Radial slits were always punched from the centre of the disk to the outside of the device but different catheter access site holes and shapes were produced. Some of these different physical embodiments of the device can be seen in FIGS. 8(*a*) to 8(*h*).

In FIG. 8(*a*) the device has a diameter of 1 inch (2.54 cm) with a 1.5 mm central access site hole and a radial slit extending outwardly from the central hole.

The device of FIG. 8(*b*) is similar to 8(*a*) but in this case there is a 4 mm central hole.

The device of FIG. 8(*c*) is also similar to 8(*a*) but in this case there is a 7 mm central hole.

The device of FIG. 8(*d*) is similar to 8(*a*) but in this case there is a T-shaped central access site.

The device of FIG. 8(*e*) has a +shaped access site whilst the device of FIG. 8(*f*) has an X shaped access site.

The device of FIG. 8(*g*) is an orthogonal shaped device with a central access site hole which may be about 4 mm and there is a radial slit.

FIG. 8(*h*) shows a rectangular shaped device with a central access site hole which may be about 4 mm and again in this case there is a radial slit.

Example 12

Microscopy Analysis of Foam Constructs

The PAGA and CHG impregnated foam dressings were also studied using microscopy to so demonstrate the impregnation of the dressing with PAGA. Thin sections of the dressing were cut with a scalpel and placed into wells of 6-well plates. 1 ml aliquots of a solution of 0.001% aqueous bromophenol blue were added to the well and allowed to stain at room temperature (RT) for 30 min. As a Negative Control, a thin section of non-impregnated foam dressing which did not contain PAGA, were similarly treated, Bromophenol blue is an acid phthalein dye, commonly used as a pH indicator and was used here for better visualization contrast of the polyurethane and PAGA due to their different pHs.

After staining for 30 min, the bromophenol blue was removed and the sections of the dressings were washed with 3 ml deionized $H_2O$. The washing was repeated three times. Images of the dressings were taken using an Olympus CKX41 microscope with an Olympus E-600 digital camera attached at a magnification of 10×. Representative images are presented in FIGS. 9(*a*) and 9(*b*). FIG. 9(*a*) shows the standard foam without active impregnation. The stained micrograph shows the cell structure of the individual cell units. FIG. 9(*b*) shows the PAGA impregnated foam. The stained PAGA particles can be seen in the micrograph along with the polyurethane foam stained cells.

Although the disclosure hereof is detailed and exact to enable those skilled in the art to practice the invention, the physical embodiments herein disclosed merely exemplify the invention that may be embodied in other ways. While the preferred embodiment has been described the details may be changed without departing from the invention.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

REFERENCES

Mital A, Fried L F and Piraino B, 2004 "Bleeding complications associated with peritoneal dialysis catheter insertion" Peritoneal Dialysis Int. 24 pp. 478-480

Doerfler M E, Kaufman B and Goldenberg A S, 1996 "Central venous catheter placement in patients with disorders of hemostasis" Chest 110 (1) pp. 185-188

Bouza E, Burillo A and Munoz, 2002 "Catheter-related infections: diagnosis and intravascular treatment" Clin. Microbial. Infect. 8: 265-274

Maki D G, Mermel L A 1998 "Infections due to infusion therapy" Taken from: Bennett J V, Brachman P S, eds. Hospital Infections. Philadelphia, Pa: Lippincott-Raven; pp. 689-724

Raad I I, Hanna H A and Darouiche R O 2001 "Diagnosis of Catheter—Related Bloodstream Infections: Is it necessary to culture the subcutaneous catheter segment?" Eur. J. Clin. Microbial. Infect. Dis. 20 pp. 566-568

Sherertz R J, Heard S O and Raad I I, 1997 "Diagnosis of triple-lumen catheter infection: Comparison of roll plate, sonication and flushing methodologies" J. Clin. Microbial. 35 pp. 641-646

Timsit J F, 2007 "Diagnosis and prevention of catheter-related infections" Curr. Opin. Crit. Care 13 (5) pp. 563-571

Lee R I and White P D "A Clinical Study of the Coagulation Time of Blood" J. Am. Med. Sci., April 1913 Vol. 245 (4), 495-503

Maki et al. "Novel Integrated Chlorhexidine-impregnated Transparent Dressing for Prevention of Vascular Catheter-related Bloodstream Infection: A Prospective Comparative Study in Healthy Volunteers", Poster Presentation at the Society for HealthCare Epidemiology of America Conference 2008, Orlando, Fla.

Bjornson, H. S., et al. 1982 "Association between microorganism growth at the catheter insertion site and colonization of the catheter in patients receiving total parenteral nutrition" Surgery, 92(4): pp. 720-727

Safdar, N. and D. G. Maki 2004 "The pathogenesis of catheter-related bloodstream infection with noncuffed short-term central venous catheters" Intensive Care Med, 30(1): pp. 62-67

Maki, D. G., et al. 1997 "Prevention of central venous catheter-related bloodstream infection by use of an antiseptic-impregnated catheter. A randomized, controlled trial" Ann Intern Med, 127(4): pp. 257-266

What is claimed is:

1. A method of making a dressing device, comprising:

forming a polyurethane foam, including:

mixing together a polyurethane prepolymer and an aqueous mixture of chlorhexidine di-gluconate and polyanhydroglucuronic acid or a salt of polyanhydroglucuronic acid in a first reaction vessel until a homogenous mixture is formed, the polyanhydroglucuronic acid or the salt thereof having a solubility in the aqueous mixture;

dispensing the homogenous mixture onto a liner; and allowing the homogenous mixture to expel carbon dioxide, thereby forming the polyurethane foam with the chlorhexidine di-gluconate and the polyanhydroglucuronic acid or the salt of polyanhydroglucuronic acid homogenously integrated into the polyurethane foam;

adhering a moisture vapor-transmissive backing to the polyurethane foam; and cutting the polyurethane foam with the moisture vapor-transmissive backing thereon to form the dressing device.

2. The method of claim 1, further comprising mixing together an isocyanate and a diol in a second reaction vessel to form the polyurethane prepolymer of the isocyanate and the diol in the second reaction vessel.

3. The method of claim 1, further comprising mixing together the chlorhexidine di-gluconate, the polyanhydroglucuronic acid or the salt of polyanhydroglucuronic acid, and water in a third reaction vessel to form the aqueous mixture.

4. The method of claim 3, wherein the aqueous mixture further includes a surfactant mixed therein, the surfactant functioning to regulate a structure of the polyurethane foam during the forming of the polyurethane foam.

5. The method of claim 4, wherein the surfactant is selected from a silicone oil, a polydimethylsiloxane-polyoxyalkylene block copolymer, and a nonylphenol ethoxylate.

6. The method of claim 3, wherein the water from the aqueous mixture reacts with isocyanate groups of at least the polyurethane prepolymer to expel the carbon dioxide and form the polyurethane foam with a desired height.

7. The method of claim 6, wherein the desired height of the polyurethane foam is 0.375 inches.

8. The method of claim 1, further comprising covering the polyurethane foam with a blanket of nitrogen; and allowing the polyurethane foam to cure and dry before adhering the moisture vapor-transmissive backing to the polyurethane foam.

9. The method of claim 1, further comprising applying an adhesive over the polyurethane foam opposite the moisture vapor-transmissive backing for adhering the dressing device to a patient.

10. The method of claim 1, wherein the polyanhydroglucuronic acid or the salt of polyanhydroglucuronic acid is present in the dressing device in an amount to achieve a haemostatic effect and the chlorhexidine di-gluconate in present in an amount to achieve an antimicrobial effect without adversely affecting wound healing.

11. The method of claim 10, wherein the polyurethane foam includes 3-20% by weight of the polyanhydroglucuronic acid or the salt of polyanhydroglucuronic acid, 9-16% by weight of the chlorhexidine di-gluconate, and a balance of the polyurethane foam itself together with a structure-regulating surfactant.

12. The method of claim 11, further comprising allowing the polyurethane foam to cure and dry before adhering the moisture vapor-transmissive backing to the polyurethane foam, the polyurethane foam including a cellular structure impregnated with particles of the salt of polyanhydroglucuronic acid upon curing and drying, the salt of polyanhydroglucuronic acid being calcium-sodium polyanhydroglucuronic acid.

* * * * *